US012232993B1

(12) United States Patent
Burnett et al.

(10) Patent No.: US 12,232,993 B1
(45) Date of Patent: *Feb. 25, 2025

(54) WEARABLE APPARATUS FOR THE TREATMENT OR PREVENTION OF OSTEOPENIA AND OSTEOPOROSIS

(71) Applicant: Bone Health Technologies, Inc., Redwood City, CA (US)

(72) Inventors: Daniel R. Burnett, San Francisco, CA (US); Shane Mangrum, Ammon, ID (US); Timothy Tigner, San Ramon, CA (US); Evan S. Luxon, Omaha, NE (US); Marcie Hamilton, San Francisco, CA (US); Alex Yee, San Francisco, CA (US); Jose Gutierrez, East Palo Alto, CA (US)

(73) Assignee: Bone Health Technologies, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/659,872

(22) Filed: May 9, 2024

Related U.S. Application Data

(63) Continuation of application No. 18/479,640, filed on Oct. 2, 2023, now Pat. No. 12,016,790, which is a
(Continued)

(51) Int. Cl.
*A61F 5/00* (2006.01)
*A61H 23/02* (2006.01)

(52) U.S. Cl.
CPC .......... *A61F 5/0003* (2013.01); *A61H 23/02* (2013.01); *A61H 23/0218* (2013.01);
(Continued)

(58) Field of Classification Search
CPC ... A61F 5/0003; A61H 23/02; A61H 23/0218; A61H 23/0245; A61H 23/0263;
(Continued)

(56) References Cited

U.S. PATENT DOCUMENTS

| 200,847 A | 3/1878 | Schmitz |
| 200,850 A | 3/1878 | Woods |

(Continued)

FOREIGN PATENT DOCUMENTS

| WO | WO 2006/060248 | 6/2006 |
| WO | WO 2007/018963 | 2/2007 |

(Continued)

OTHER PUBLICATIONS

Addington et al., Intra-abdominal Pressures during Voluntary and Reflex Cough, BioMed Central, Cough 2008, 4:2, Apr. 30, 2008.
(Continued)

*Primary Examiner* — Garrett K Atkinson
(74) *Attorney, Agent, or Firm* — Levine Bagade Han LLP

(57) ABSTRACT

A wearable apparatus for the treatment or prevention of osteopenia or osteoporosis, stimulating bone growth, preserving or improving bone mineral density, and inhibiting adipogenesis is disclosed where the apparatus may generally comprise one or more vibrating elements configured for imparting repeated mechanical loads to the hip, femur, and/or spine of an individual at a frequency and acceleration sufficient for therapeutic effect. These vibrating elements may be secured to the upper body of an individual via one or more respective securing mechanisms, where the securing mechanisms are configured to position the one or more vibrating elements in a direction lateral to the individual, and the position, tension, and efficacy of these vibrating elements may be monitored and/or regulated by one or more accelerometers.

16 Claims, 7 Drawing Sheets

Related U.S. Application Data continuation of application No. 17/544,783, filed on Dec. 7, 2021, now Pat. No. 11,806,262, which is a continuation of application No. 17/093,453, filed on Nov. 9, 2020, now Pat. No. 11,219,542, which is a continuation of application No. 16/239,305, filed on Jan. 3, 2019, now Pat. No. 11,026,824, which is a continuation of application No. 14/736,077, filed on Jun. 10, 2015, now Pat. No. 10,206,802, which is a continuation of application No. PCT/US2013/074296, filed on Dec. 11, 2013.

(60) Provisional application No. 61/797,844, filed on Dec. 17, 2012, provisional application No. 61/873,246, filed on Sep. 3, 2013.

(52) U.S. Cl.
CPC ..... *A61H 23/0245* (2013.01); *A61H 23/0263* (2013.01); *A61H 2201/1445* (2013.01); *A61H 2201/1623* (2013.01); *A61H 2201/1628* (2013.01); *A61H 2201/1633* (2013.01); *A61H 2201/1635* (2013.01); *A61H 2201/164* (2013.01); *A61H 2201/165* (2013.01); *A61H 2201/5002* (2013.01); *A61H 2201/5005* (2013.01); *A61H 2201/501* (2013.01); *A61H 2201/5012* (2013.01); *A61H 2201/5061* (2013.01); *A61H 2201/5084* (2013.01); *A61H 2201/5097* (2013.01); *A61H 2205/081* (2013.01); *A61H 2205/088* (2013.01)

(58) Field of Classification Search
CPC .... A61H 2201/1445; A61H 2201/1623; A61H 2201/1628; A61H 2201/1633; A61H 2201/1635; A61H 2201/164; A61H 2201/165; A61H 2201/5002; A61H 2201/5005; A61H 2201/501; A61H 2201/5012; A61H 2201/5061; A61H 2201/5084; A61H 2201/5097; A61H 2205/081; A61H 2205/088
See application file for complete search history.

(56) References Cited

U.S. PATENT DOCUMENTS

| | | |
|---|---|---|
| 3,326,207 A | 6/1967 | Egan |
| 4,077,394 A | 3/1978 | Mccurdy |
| 4,413,633 A | 11/1983 | Yanda |
| 4,502,490 A | 3/1985 | Evans et al. |
| 4,570,927 A | 2/1986 | Petrofsky et al. |
| 4,600,015 A | 7/1986 | Evans et al. |
| 4,712,566 A | 12/1987 | Hok |
| 4,841,981 A | 6/1989 | Tanabe et al. |
| 5,035,231 A | 7/1991 | Kubokawa et al. |
| 5,048,532 A | 9/1991 | Hickey |
| 5,158,529 A | 10/1992 | Kanai |
| 5,171,299 A | 12/1992 | Heitzmann et al. |
| 5,220,927 A | 6/1993 | Astrahan et al. |
| 5,240,675 A | 8/1993 | Wilk et al. |
| 5,344,435 A | 9/1994 | Turner et al. |
| 5,389,217 A | 2/1995 | Singer |
| 5,398,692 A | 3/1995 | Hickey |
| 5,413,558 A | 5/1995 | Paradis |
| 5,425,362 A | 6/1995 | Siker et al. |
| 5,427,114 A | 6/1995 | Colliver et al. |
| 5,431,628 A | 7/1995 | Millar |
| 5,433,216 A | 7/1995 | Sugure et al. |
| 5,478,329 A | 12/1995 | Ternamian |
| 5,570,671 A | 11/1996 | Hickey |
| 5,865,801 A | 2/1999 | Houser |
| 5,902,248 A | 5/1999 | Millar et al. |
| 5,916,153 A | 6/1999 | Rhea, Jr. |
| 5,921,935 A | 7/1999 | Hickey |
| 6,001,600 A | 12/1999 | Hodgson et al. |
| 6,083,215 A | 7/2000 | Milavetz |
| 6,149,578 A | 11/2000 | Downey et al. |
| 6,287,253 B1 | 9/2001 | Ortega et al. |
| 6,434,418 B1 | 8/2002 | Neal et al. |
| 6,447,462 B1 | 9/2002 | Wallace et al. |
| 6,602,243 B2 | 8/2003 | Noda |
| 6,616,597 B2 | 9/2003 | Schock et al. |
| 6,648,906 B2 | 11/2003 | Lasheras et al. |
| 6,666,828 B2 | 12/2003 | Greco et al. |
| 6,866,644 B1 | 3/2005 | Kost |
| 6,912,416 B2 | 6/2005 | Rosenblatt |
| 6,916,283 B2 | 7/2005 | Tracey et al. |
| 6,918,924 B2 | 7/2005 | Lasheras |
| 6,931,276 B2 | 8/2005 | Streng et al. |
| 6,997,884 B2 | 2/2006 | Ulmsten et al. |
| 7,004,899 B2 | 2/2006 | Tracey |
| 7,025,718 B2 | 4/2006 | Williams |
| 7,052,452 B2 | 5/2006 | Ulmsten et al. |
| 7,112,177 B2 | 9/2006 | Christensen et al. |
| 7,252,631 B2 | 8/2007 | Tracey |
| 7,255,673 B2 | 8/2007 | Ulmsten et al. |
| 7,381,190 B2 | 6/2008 | Sugure et al. |
| 7,402,144 B2 | 7/2008 | Mcleod |
| 7,409,240 B1 | 8/2008 | Bishop |
| 7,462,158 B2 | 12/2008 | Mor |
| 7,597,101 B2 | 10/2009 | Burnett et al. |
| 7,644,722 B2 | 1/2010 | Christensen et al. |
| 7,727,147 B1 | 6/2010 | Osorio et al. |
| 7,850,704 B2 | 12/2010 | Burnett et al. |
| 7,892,181 B2 | 2/2011 | Christensen et al. |
| 7,955,282 B2 | 6/2011 | Doo |
| 8,052,671 B2 | 11/2011 | Christensen et al. |
| 8,273,036 B2 | 9/2012 | Fong |
| 8,285,399 B2 | 10/2012 | Van Bommel et al. |
| 8,337,411 B2 | 12/2012 | Nishtala et al. |
| 8,384,907 B2 | 2/2013 | Tearney et al. |
| 8,396,537 B2 | 3/2013 | Balji et al. |
| 9,044,375 B2 | 6/2015 | Reyes General et al. |
| 11,026,824 B2 | 6/2021 | Burnett et al. |
| 11,219,542 B2 | 1/2022 | Burnett et al. |
| 11,806,262 B2 | 11/2023 | Burnett et al. |
| 2001/0020162 A1 | 9/2001 | Mosel et al. |
| 2001/0035046 A1 | 11/2001 | Williams |
| 2002/0055731 A1 | 5/2002 | Atala et al. |
| 2002/0068860 A1 | 6/2002 | Clark |
| 2003/0187392 A1 | 2/2003 | Egger |
| 2003/0032904 A1 | 9/2003 | Grim et al. |
| 2004/0082859 A1 | 4/2004 | Schaer et al. |
| 2004/0097813 A1 | 5/2004 | Williams |
| 2004/0220682 A1 | 11/2004 | Levine et al. |
| 2004/0236395 A1 | 11/2004 | Iaizzo et al. |
| 2005/0107855 A1 | 5/2005 | Lennox et al. |
| 2005/0216054 A1 | 9/2005 | Widomski et al. |
| 2005/0251068 A1 | 11/2005 | Mor |
| 2006/0015045 A1 | 1/2006 | Zets et al. |
| 2006/0100743 A1 | 5/2006 | Townsend et al. |
| 2006/0135889 A1 | 6/2006 | Egli |
| 2006/0189905 A1 | 8/2006 | Eischen |
| 2006/0234383 A1 | 10/2006 | Gouch |
| 2006/0282175 A1 | 12/2006 | Haines et al. |
| 2007/0032733 A1 | 2/2007 | Burton |
| 2007/0038143 A1 | 2/2007 | Christensen et al. |
| 2007/0203396 A1 | 8/2007 | McCutcheon et al. |
| 2007/0237739 A1 | 10/2007 | Doty |
| 2007/0255167 A1 | 11/2007 | Christensen et al. |
| 2008/0097471 A1 | 4/2008 | Adams et al. |
| 2008/0139979 A1 | 6/2008 | Talish et al. |
| 2008/0177232 A1 | 7/2008 | Knighton et al. |
| 2008/0200847 A1 | 8/2008 | Bernstein |
| 2008/0200850 A1 | 8/2008 | Casalino |
| 2009/0076573 A1 | 3/2009 | Burnett et al. |
| 2009/0112134 A1 | 4/2009 | Avni |
| 2009/0187164 A1 | 7/2009 | Rowe |
| 2009/0221933 A1 | 9/2009 | Nishtala et al. |
| 2009/0308588 A1 | 12/2009 | Howell et al. |
| 2009/0312740 A1 | 12/2009 | Kim et al. |

(56) References Cited

U.S. PATENT DOCUMENTS

| | | |
|---|---|---|
| 2010/0030133 A1 | 2/2010 | Elia et al. |
| 2010/0099993 A1 | 4/2010 | Cohen et al. |
| 2010/0121220 A1 | 5/2010 | Nishtala |
| 2010/0160834 A1 | 6/2010 | Fong |
| 2010/0204765 A1 | 8/2010 | Hall et al. |
| 2010/0228148 A1 | 9/2010 | Kim |
| 2011/0054488 A1 | 3/2011 | Gruber et al. |
| 2011/0071482 A1 | 3/2011 | Selevan |
| 2011/0118555 A1 | 5/2011 | Dhumne et al. |
| 2011/0144423 A1 | 6/2011 | Tong et al. |
| 2011/0301514 A1 | 12/2011 | Reyes General et al. |
| 2012/0022415 A1 | 1/2012 | Mullen et al. |
| 2013/0023731 A1 | 1/2013 | Saadat et al. |
| 2013/0030262 A1 | 1/2013 | Burnett et al. |
| 2014/0163439 A1 | 6/2014 | Uryash et al. |
| 2015/0328081 A1 | 11/2015 | Goldenberg et al. |
| 2019/0133801 A1 | 5/2019 | Burnett et al. |
| 2021/0052407 A1 | 2/2021 | Burnett et al. |
| 2022/0087844 A1 | 3/2022 | Burnett et al. |
| 2024/0024142 A1 | 1/2024 | Burnett et al. |

FOREIGN PATENT DOCUMENTS

| | | |
|---|---|---|
| WO | WO 2008/097609 | 8/2008 |
| WO | WO 2008/103625 | 8/2008 |
| WO | WO 2009/055435 | 4/2009 |
| WO | WO 2010/141503 | 12/2010 |
| WO | WO 2012/056084 | 5/2012 |
| WO | WO 2012/056484 | 5/2012 |
| WO | WO 2012/122267 | 9/2012 |
| WO | WO 2013/106155 | 7/2013 |

OTHER PUBLICATIONS

Beck et al., The Effect of 8 Mos of Twice-Weekly Low- or Higher Intensity Whole Body Vibration on Risk Factors for Postmenopausal Hip Fracture, American Journal of Physical Medicine 7 Rehabilitation, 89(12): 997-1009, Dec. 2010.

Reyes, et al., High-Frequency, Low-Intensity Vibrations Increase Bone Mass and Muscle Strength in Upper Limbs, Improving Autonomy in Disabled Children, Journal of Bone and Mineral Research, 26(8), 1759-1766, 2011.

Rubin et al. Adipogenesis is inhibited by brief, daily exposure to high-frequency, extremely low-magnitude mechanical signals. PNAS. Nov. 6, 2007; 04(45):17879-17884.

Rubin et al., Prevention of Postmenopausal Bone Loss By a Low-Magnitude, High-Frequency Mechanical Stimuli: A Clinical Trial Assessing Compliance, Efficacy, and Safety, Journal of Bone and Mineral Research, 19:343-351, Dec. 22, 2003.

Rubin et al., Transmissibility of 15-Hertz to 35-Hertz Vibrations to the Human Hip and Lumbar Spine: Determining the Physiologic Feasibility of Delivering Low-Level Anabolic Mechanical Stimuli to Skeletal Regions at Greatest Risk of Fracture Because of Osteoporosis. Spine, 28:2621-2627, 2003.

Slatkovska et al. Effect of 12 Months of Whole-Body Vibration Therapy on Bone Density and Structure in Postmenopausal Women. Ann Intern Med., 155(10):668-79, Nov. 15, 2011.

Song et al. Whole Body Vibration Effects on Body Composition in the Postmenopausal Korean Obese Women: Pilot Study. Korena J Fam Med. 2011; 32:399-405.

Verschueren et al. Effect of 6-Month Whole Body Vibration Training on Hip Density, Muscle Strength, and Postural Control in Postmenopausal Women: A Randomized Controlled Pilot Study. Journal of Bone and Mineral Research, 19:352-359, 2004.

WEARABLE APPARATUS FOR THE TREATMENT OR PREVENTION OF OSTEOPENIA AND OSTEOPOROSIS

CROSS-REFERENCE TO RELATED APPLICATIONS

This application is a continuation of U.S. patent application Ser. No. 18/479,640 filed Oct. 2, 2023, which is a continuation of U.S. patent application Ser. No. 17/544,783 filed Dec. 7, 2021 (now U.S. Pat. No. 11,806,262 issued Nov. 7, 2023), which is a continuation of U.S. patent application Ser. No. 17/093,453 filed Nov. 9, 2020 (now U.S. Pat. No. 11,219,542 issued Jan. 11, 2022), which is a continuation of U.S. patent application Ser. No. 16/239,305 filed Jan. 3, 2019 (now U.S. Pat. No. 11,026,824 issued Jun. 8, 2021), which is a continuation U.S. patent application Ser. No. 14/736,077 filed Jun. 10, 2015 (now U.S. Pat. No. 10,206,802 issued Feb. 19, 2019), which is a continuation of International Application No. PCT/US2013/074296 filed Dec. 11, 2013, which claims the benefit of priority to U.S. Provisional Patent Application Nos. 61/797,844 filed Dec. 17, 2012 and 61/873,246 filed Sep. 3, 2013, each of which is incorporated herein by reference in its entirety.

This application is further related to U.S. Provisional Patent Application Nos. 61/464,619 filed Mar. 7, 2011 and 61/744,030 filed Sep. 17, 2012; U.S. patent application Ser. No. 13/414,011 filed Mar. 7, 2012 and Ser. No. 13/414,307 filed Mar. 7, 2012; and International Application Nos. PCT/US2012/028071 filed Mar. 7, 2012 and PCT/US2012/069262 filed Dec. 12, 2012, each of which is incorporated herein by reference in its entirety.

FIELD OF THE INVENTION

The present invention relates generally to the stimulation of bone growth, healing of bone tissue, and treatment and prevention of osteopenia, osteoporosis, and chronic back pain, and to preserving or improving bone mineral density, and to inhibiting adipogenesis particularly by the application of repeated mechanical loading to bone tissue.

BACKGROUND OF THE INVENTION

Low bone mineral density (BMD) and osteoporosis are significant problems facing the elderly, leading to 1.5 million fractures in 2002 (National Osteoporosis Foundation (NOF): America's bone health: The state of osteoporosis and low bone mass in our nation. Washington DC, National Osteoporosis Foundation, 2002). Bisphosphonates, a class of compounds that generally inhibit the digestion of bone, have been used for over a decade to treat osteoporosis with significant success but cause unwanted side effects including osteonecrosis of the jaw, erosion of the esophagus, and atypical femoral fractures, which has lead to the reconsideration of the use of bisphosphonate therapy.

One alternative to treat osteoporosis has been the use of Whole Body Vibration (WBV), which consists of repeated mechanical loading of bone tissue through vibration devices, using relatively high frequencies (e.g. 15-90 Hz) and relatively low mechanical loads (e.g. 0.1-1.5 g's). Studies have shown that WBV can delay and/or halt the progression of osteoporosis (Rubin et. al., Journal of Bone and Mineral Research, 19:343-351, 2004). In another randomized study, in which ≥0.6 g's of vibratory force were delivered to the feet of the patient, it was demonstrated that WBV was effective in improving hip BMD outcomes as compared to control groups that either did not exercise or were part of an exercise program (Verschueren et al., Journal of Bone and Mineral Research, 19:352-359, 2004).

Related studies have demonstrated the ability of WBV to improve hip and preserve spine BMD in populations of healthy cyclists, postmenopausal women and disabled children (Am J Phys Med Rehabil 2010; 89:997-1009, Ann Intern Med 2011; 155:668-679, J Bone and Mineral Research 2011; 26(8):1759-1766).

The mechanism by which WBV influences BMD is an issue of some debate but studies have suggested that the shear stress within bone marrow in trabecular architecture during high frequency vibration could provide the mechanical signal to marrow cells that leads to bone anabolism (Journal of Biomechanics 45(2012):2222-2229). More specifically, shear stress above 0.5 Pa is mechanostimulatory to osteoblasts, osteoclasts and mesenchymal stem cells (Journal of Biomechanics 45(2012):2222-2229).

Many conventional methods of promoting bone tissue growth and bone maintenance by the application of WBV generally tend to apply relatively high frequency (e.g. 15-90 Hz) and relatively low magnitude mechanical loads (e.g. 0.1-1.5 g's) to bodily extremities, such as the use of vibrating platforms upon which a user stands that apply repeated mechanical loads to the feet of a user. Current WBV vibration platforms (e.g. Galileo 900/2000™, Novotec Medical, Pforzheim, Germany; or Power Plate™, Amsterdam, The Netherlands) and associated treatment regimens require the user to stand on a platform for up to 30 minutes a day, which is inconvenient for many users. Furthermore, applying vibration to the feet of the patient is an inefficient method for mechanically loading the hips, femur, and spine, the targeted areas for WBV therapy for osteoporosis. Up to 40% of vibration power is lost between the feet and the hips and spine due to mechanical damping in the knees and ankles (Rubin et al., Spine (Phila Pa 1976), 28:2621-2627, 2003).

One other issue with current WBV platforms is the directionality of applied force. Standing on a vibrating platform, an individual receives WBV stimulus in a plane perpendicular to the spine and long bones of hip. Studies have shown that vibrations applied "in the inferior-superior direction would be misaligned with the principal trabecular orientation in the greater trochanter and femoral neck, resulting in lower shear. In contrast, trabeculae in the lumbar spine are aligned with the direction of vibration and the permeability is higher (Journal of Biomechanics 45(2012): 2222-2229).

There is a need for a more efficient and easy to use source of mechanical vibration that delivers 0.6 g+/−0.5 g of force directly to the spine and hips. A more efficient method for delivering vibration force would be to reduce the load applied to the patient and make the device easier to use, while maximizing therapeutic benefit to osteoporosis by localizing the repeated mechanical loads delivered to the hip and spine. Additionally, the potential to deliver WBV in a plane parallel to the directionality of the spine and long bones of the hip may be more beneficial than a traditional vibrating plate on which a person stands.

Finally, the existing technology of vibrating platforms limits the application of WBV to special populations that may benefit from its use. Cyclists, for example, have been shown to have lower BMD than other athletes and even lower than the BMD of sedentary people (Int J Sports Med 2012; 33:593-599). Thus, a wearable delivery system for this technology extends the reach of this tool to a wider population of individuals. Not only could a wearable device be used during cycling (or other activities), the present invention could be adapted to deliver WBV through a bicycle to the rider for the purpose of preserving BMD in cyclists.

In a separate but connected issue, WBV have been suggested to be "anabolic to the musculoskeletal system" and "in parallel, suppress adiposity" (PNAS. Nov. 6, 2007; 104(45):17879-17884). In animal models, studies have shown that low magnitude WBV can reduce stem cell adipogenesis and can provide a tool for "nonpharmacologic prevention of obesity and its sequelae" (PNAS. Nov. 6, 2007; 104(45):17879-17884). In a study done with obese women, WBV displayed a "positive effect on body weight and waist circumference reduction" (Korena J Fam Med. 2011; 32:399-405).

SUMMARY OF THE INVENTION

The present invention seeks to provide a novel method and apparatus for the stimulation of bone growth, healing of bone tissue, and prevention of osteoporosis, osteopenia, and chronic back pain, as is described more in detail hereinbelow. The present invention may maintain or promote bone-tissue growth, may prevent the onset of osteoporosis, and may treat chronic back pain.

Contrary to the prior art, which attempts to induce WBV to the subject while standing on a vibration platform or through other application of WBV to bodily extremities, the present invention provides more effective treatment by targeted application of oscillating mechanical loads to the hip and spine of a user, as is described hereinbelow.

What is more, in distinction from the prior art, the present invention allows for delivery of WBV stimulus in side-to-side, front-to-back, and/or in an inferior-superior directions. This flexibility in the delivery system and the potential to load the bones of the spine and hips in more than just an inferior-superior plane (as is the case with a vibrating platform), may allow for better targeting of the hips and spine in the treatment of osteoporosis and loss of BMD. More specifically in one variation, one or more vibrating elements may be positioned against the patient's body via one or more securing mechanisms, respectively, which are configured to position the vibrating elements in a direction lateral to the individual's body such that the mechanical loads are applied laterally to the patient rather than in an inferior-superior direction.

In one aspect of the present invention, a wearable apparatus for treating osteoporosis and supporting BMD is provided, comprising one or more vibrating elements configured for imparting repeated mechanical loads to the hip and spine of an individual at a frequency and acceleration sufficient for therapeutic effect on osteoporosis; and one or more securing mechanisms for securing said one or more vibrating elements to the upper body of said individual; wherein said one or more vibrating elements are configured for applying said repeated mechanical loads to said individual's hip and spine.

In one embodiment of the present invention, the securing mechanisms of the apparatus attach to the shoulders of an individual to apply vibration to the back of the individual. In another aspect, additional securing mechanisms attach to the waist of the individual to provide additional support to the apparatus while it applies vibration to the back of the individual. In another embodiment, the securing mechanisms attach only to the waist or hips of an individual to apply vibration in those locations. The location of applied vibration can thus be adjusted to preferentially deliver vibration to the spine, hips, or other locations.

In another aspect of the present invention, the device is worn around the waist of the individual such that the vibrating element delivers vibration to the lower abdomen or lower back of the individual. This placement maximizes the transmission of vibration to both the spine and the hip.

In another aspect of the invention, the device can be configured to be worn around other parts of the body, including extremities such as the arms, legs, hand, feet, and head. This configuration is preferably a scaled-down version of the embodiment to be worn around the spine, waist, or hips.

In another embodiment, the apparatus further comprises a manually settable control for adjusting the frequency of said repeated mechanical loads provided by said one or more vibrating elements. In another embodiment, the apparatus further comprises a manually settable control for adjusting the peak acceleration provided by said one or more vibrating elements.

In another embodiment, the peak acceleration is adjustable based on closed-loop feedback from accelerometers around the patient's hips, spine, or other sites of interest. The vibrating elements are programmed to slowly increase the acceleration until the desired level is reached, then maintain that level for the rest of the treatment. In another aspect, the accelerometers are disposable, which ensures performance and provides a recurring revenue stream for the company. In another aspect, the accelerometers are permanently mounted inside the pack itself.

In another embodiment, the relative readings of the various accelerometers ensure that the device is properly positioned and/or tensioned.

In another embodiment, the straps of the pack have force/tension sensors in order to ensure the patient has securely attached the device before beginning treatment.

In another embodiment, said vibrating element comprises an oscillating element energized by an electrical power source. In another embodiment, said oscillating element comprises an oscillating mass that moves in a periodic motion. In another embodiment, said vibrating element vibrates at a frequency in a range of about 15-90 Hz. In another embodiment, said vibrating element generates peak acceleration in a range of about 0.1-1.5 g. In another embodiment, said vibrating element is operative to induce strain in bone tissue in a range of about 1-500 microstrain. In another embodiment, said vibrating element is operative to induce strain in bone tissue in a range of about 20-50 microstrain.

In another aspect of the invention, the pack has an internal timer that tracks the length of treatment and automatically turns the device off after the treatment is complete. This feature can also be used to prevent excessive use of the device.

In another embodiment, the pack has internal memory which is used to log the use of the device. Additionally, the pack has wired and/or wireless connectivity to other devices that can communicate with the patient, the patient's family, and/or the patient's doctor. The other devices can be computers, phones, tablets, watches, or any other similar device capable of displaying and sensing information. Logging information can be used to track compliance and provide reminders to the patient when it is time for a treatment session. This information can also be used as part of a points-base rewards system to encourage the patients to use the device.

In another aspect of the present invention, a method for treating osteoporosis is provided, comprising securing one or more vibrating elements to the upper body of an individual, wherein said one or more vibrating elements are configured to impart repeated mechanical loads to the hip and spine of said individual at a frequency and acceleration sufficient for therapeutic effect on osteoporosis; and wherein said one or more vibrating elements may impart said repeated mechanical loads during said individual's ambulation.

One embodiment of the present invention would include a mechanism for delivering WBV through a bicycle to the rider for the prevention of osteoporosis and supporting BMD.

Additionally, the present invention provides a wearable tool to use WBV for the purpose of weight loss and decreasing adipogenesis.

INCORPORATION BY REFERENCE

All patents, patent applications, and other publications referred to herein are expressly incorporated by reference, to the same extent as if each individual publication, patent or patent application was specifically and individually indicated to be incorporated by reference. All documents cited are, in relevant part, incorporated herein by reference. However, the citation of any document is not to be construed as an admission that it is prior art with respect to the present invention.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

The present invention provides methods and apparatuses for the stimulation of bone growth, healing of bone tissue, and treatment and prevention of osteopenia, osteoporosis, and chronic back pain.

Exemplary embodiments of the apparatus of the present invention are illustrated in FIGS. 1-7 as follows.

Figure 1:
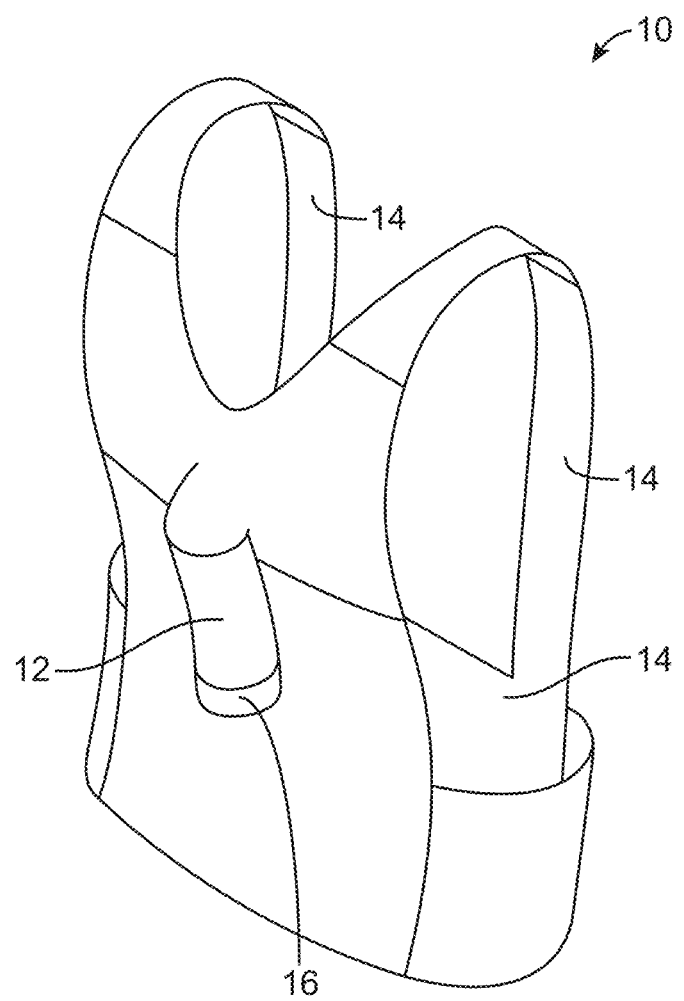
FIG. 1 is an illustration of an exemplary embodiment of the present invention from an angled rear perspective.

FIG. 1 illustrates an apparatus for the stimulation of bone growth, prevention of osteopenia, healing of bone tissue, and treatment and prevention of osteopenia, osteoporosis, and chronic back pain 10, constructed and operative in accordance with an embodiment of the present invention. The apparatus 10 may include a vibrating element configured for imparting repeated mechanical loads to the hip and spine of an individual at a frequency and acceleration sufficient for therapeutic effect on osteoporosis 12. The vibrating element 12 may be secured to the upper body of an individual through one or more securing mechanisms 14. In such an arrangement, the vibrating element 12 may be configured for applying repeated mechanical loads to an individual's hip and spine.

Securing mechanisms 14 may be constructed in any shape and of any suitable material. For example, the securing mechanisms 14 may be made of any elastomeric material, such as but not limited to, cloth, woven or non-woven, natural or synthetic rubber, silicone rubber, polyurethane, nylon, or polyester, with one or more enclosures for containing the vibrating element 12. The securing mechanisms 14 may be in the form of a vest and may include one or more sleeves or shoulder straps for the upper extremities of the subject. The securing mechanisms may fasten the vibrating element 12 to the torso of an individual in any manner, such as but not limited to, VELCRO, hooks, buckles, buttons, zippers, tying (e.g. laces), adhesive, and the like. The securing mechanisms may also attach to the shoulders, chest, abdomen, waist, hips, arms, legs, hands, feet, or head of an individual. The vibrating element 12 does not have to be contained within an enclosure, and may be attached in any other manner to the securing mechanisms 14, such as but not limited to, by bonding, embedding, etc. The securing mechanisms 14 may have any length, width and thickness.

Optionally, electronics may be embedded in the apparatus such that the electronics enable communication between the apparatus and another device (e.g., a server, computer, communications device, smart phone, etc.) which may be remotely located. The electronics may be configured to track and/or report compliance with a prescribed or recommended usage through wired or wireless protocols for reporting or communicating with the other device.

The vibrating element 12 may be configured for imparting repeated mechanical loads through any means known in the present art. The vibrating element 12 may include an oscillating element energized by an electrical power source. For example, an electromagnetic weight may be attached to a spring which is mounted for oscillating motion inside the vibrating element 12 and alternately attracted and repelled by a surrounding frame made of ferrous material, that is, an oscillating mass that moves in a periodic motion. It is understood that this is just one example of the vibrating element 12 being energized by an electrical power source 16. Another example of a vibrating element is an ultrasonic transducer that induces vibration of desired amplitude. Yet another example of a vibrating element is a slider-crank mechanism (e.g. as described in Zhang, Y. "Introduction to Mechanisms", Carnegie Mellon University). Yet another example of a vibrating element is an eccentric mass attached to a motor that creates vibrations as it rotates.

The vibrating element may also be configured to impart repeated mechanical loads in such a way that the frequency and amplitude of acceleration are decoupled. In one embodiment, the vibrating element makes use of a clutch mechanism which is able to adjust the amplitude of the acceleration while the frequency remains constant. In another embodiment, the element makes use of a motor and eccentric weight attached to an adjustable-length moment arm. By adjusting the length of this moment arm, the amplitude of the acceleration can be adjusted independently of the frequency. In yet another embodiment, multiple eccentric motors are used and designed to have interference that is either constructive, destructive, or mixed. Depending on the setting, the motors are either be in phase, out of phase, or somewhere in between, which allows the amplitude of the acceleration to be adjusted while maintaining a constant frequency.

The vibrating element 12 may be configured for imparting repeated mechanical loads to the hip and spine of an individual at a frequency of between about 1-200 Hz and a peak acceleration of between about 0.1-10 g (where g=9.8 m/s) to induce strain in bone tissue of an individual in a range of about 1-500 microstrain. Alternatively, the vibrating element 12 may vibrate at a frequency in a range of about 1-100 Hz, about 1-50 Hz, about 5-35 Hz, about 20-50 Hz, or about 15-45 Hz. Alternatively, the vibrating element 12 may impart repeated mechanical loads at a peak acceleration of between about 0.1-5 g, about 0.3-1.5 g, about 0.6-1.5 g, or about 0.6 g. Alternatively, the vibrating element 12 may induce strain in bone tissue in a range of about 50-500 microstrain, about 1-250 microstrain, about 1-100 microstrain, or about 100 microstrain. However, the present invention is not limited to these values and other ranges of amplitude and frequency may be used.

The frequency of the applied repeated mechanical loads provided by the vibrating element 12 may be adjusted by an individual by a manually settable control. Alternatively, the peak acceleration of repeated mechanical loads imparted by the vibrating element 12 may be adjusted by an individual by a manually settable control. The vibrating element 12 may be capable of being adjusted to any value or range of frequency or peak acceleration as desired. The manually settable control may be in the form of a rotating dial, one or more push buttons, one or more switches, or a computer interface. Additionally, the vibrating element 12 may be suitably comfortable enough for patients to wear up to 10 minutes (or longer) at a time.

The electrical power source 16 may be a battery (which may be rechargeable) disposed in the vibrating element 14. Alternatively, the electrical power source 16 may be external to the apparatus 10, such as but not limited to, AC power or other power supply, and may be in wired (e.g., connected by an electrical range cord or any other kind of electrical connector or terminal) or wireless (e.g., radio frequency (RF), infrared, laser, Bluetooth, etc.) communication with the vibrating element 12. In the case of a battery, a status LED or other means of alert can be used to inform the user when the battery needs to be replaced or charged.

Figure 2:
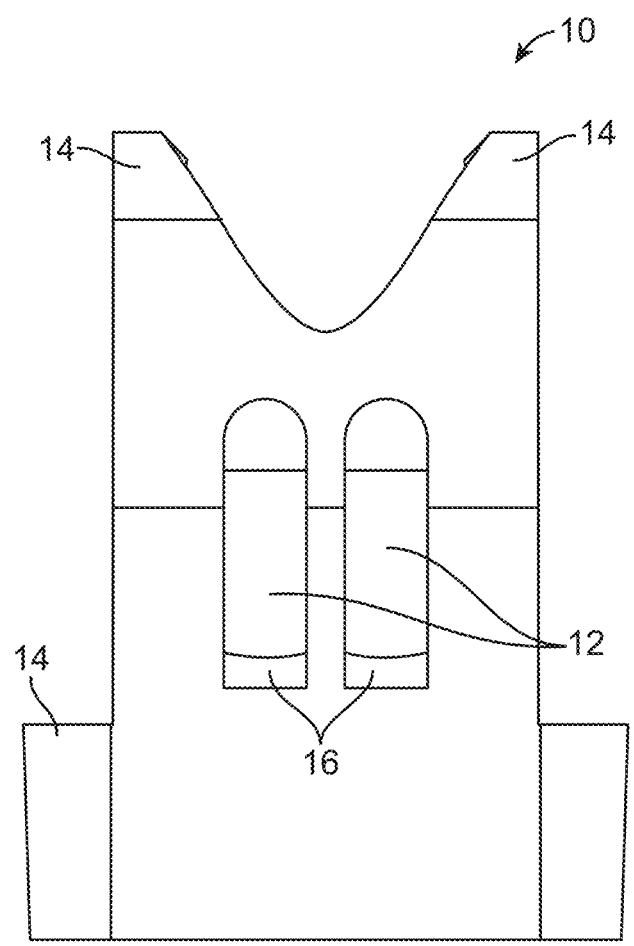
FIG. 2 is an illustration of an exemplary embodiment of the present invention with two vibrating elements from the rear perspective.

FIG. 2 illustrates the apparatus 10 with multiple vibrating elements 12. The apparatus 10 may contain one, two, three, four, five, or more than five vibrating elements 12.

Figure 3:
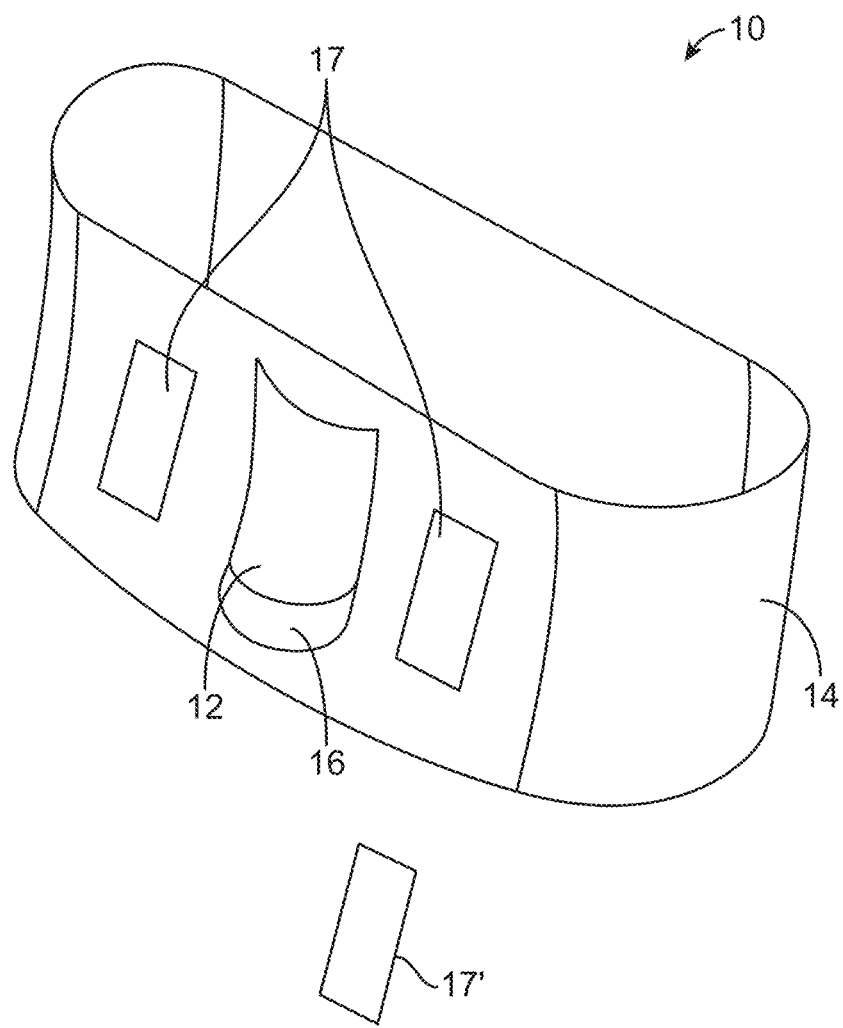
FIG. 3 is an illustration of an exemplary embodiment of the present invention from an angled rear perspective.

FIG. 3 illustrates the apparatus 10 with securing mechanisms 14 that attach only to the waist or hips of an individual. This embodiment still comprises at least one vibrating element 12 and electrical power source 16.

Figure 4:
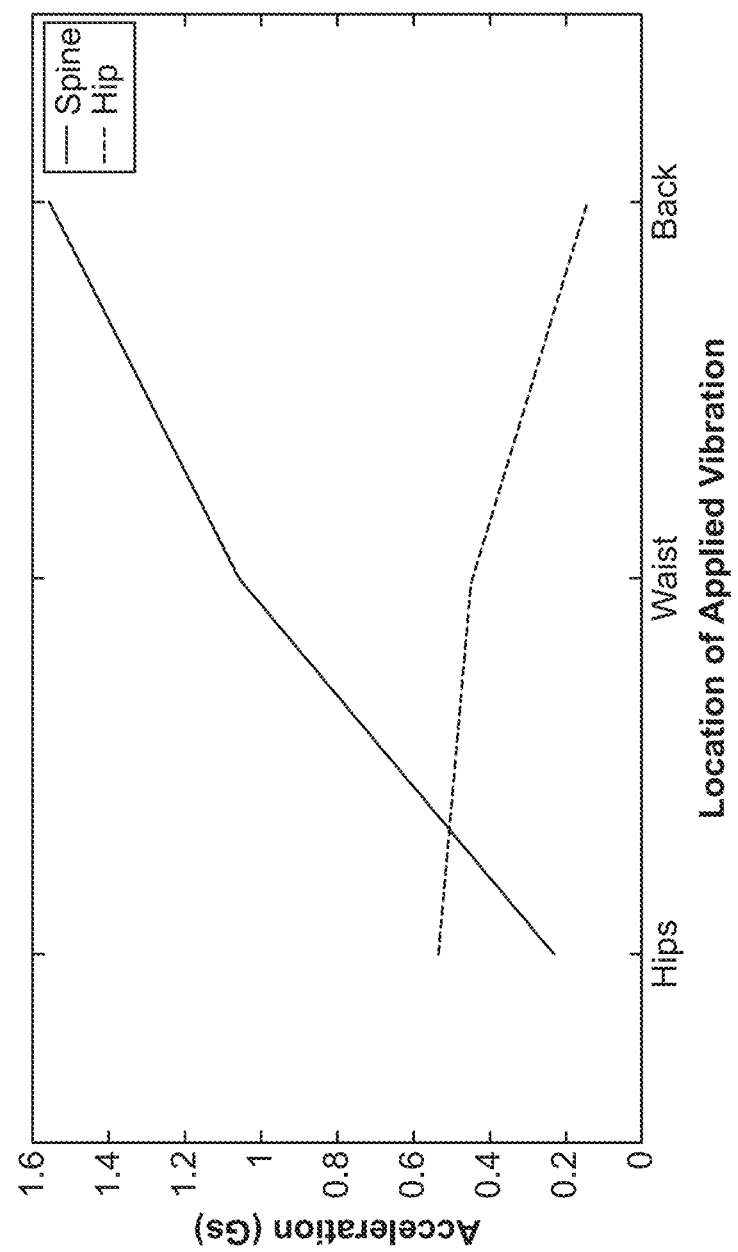
FIG. 4 is a graph illustrating the ability to preferentially apply vibration to the spine or hips depending on where the present invention is worn.

FIG. 4 illustrates the ability to preferentially deliver vibration to the spine, hips, or other locations, depending on where the present invention is worn. The data were collected by attaching accelerometers to the skin directly superficial to the iliac crest (hip) and T7 vertebra (spine) of a test subject, while the present invention was worn on the back, waist and hips of the subject. When worn on the back, vibrations are preferentially delivered to the spine of the individual. When worn on the hips, vibrations are preferentially delivered to the hips of the individual. When worn on the waist, vibrations are preferentially delivered to the spine of the individual, although significant vibrations are also delivered to the hip. Therefore, the preferred embodiment of the present invention is to be worn around the waist of an individual. More specifically, the invention should be placed over the lower abdomen and lower back to maximize transmission of vibration to both the spine and the hip.

Figure 5A:
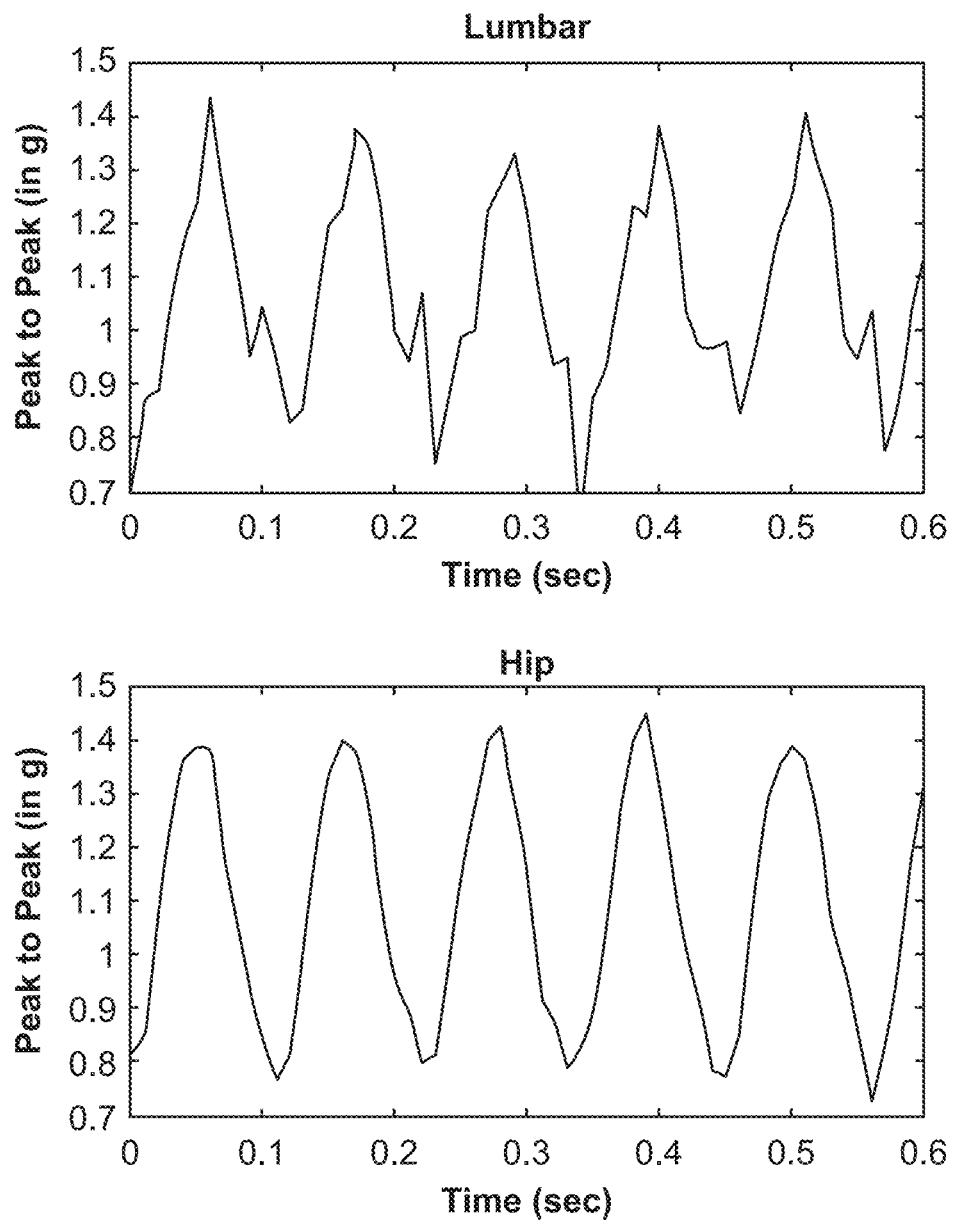
FIGS. 5A and 5B are graphs illustrating accelerations experienced at the hip and lumbar spine during normal use of the present invention.

FIG. 5A further illustrates the accelerations experienced at the hip and lumbar spine during normal use of the present invention. With the device properly positioned, acceleration magnitudes of around 0.6 g are delivered, as measured by skin-mounted accelerometers.

The present invention may stimulate bone growth, maintain bone tissue, preserve or improve bone mineral density, and prevent osteoporosis and osteopenia in various bone regions of the hip (e.g. femoral head, femoral neck, greater trochanter, lesser trochanter, femur, anterior superior iliac spine, etc.) and spine (e.g. cervical spine, thoracic spine, lumbar spine, sacrum, coccyx, etc.). Alternatively, the present invention may stimulate bone growth in bones in other parts of the body, as the vibrations carry to other parts of the body (e.g., bones in the vicinity of the legs, knees, or feet). Stimulation to other sites can also be accomplished by using a scaled-down version of the present device to directly stimulate the legs, arms, feet, hands, head, or any other location.

In order to determine the vibration levels that the patient receives when wearing the apparatus 10, accelerometers may be used with the patient. For instance, bone-mounted accelerometers may be used although invasive to the patient.

Figure 5B:
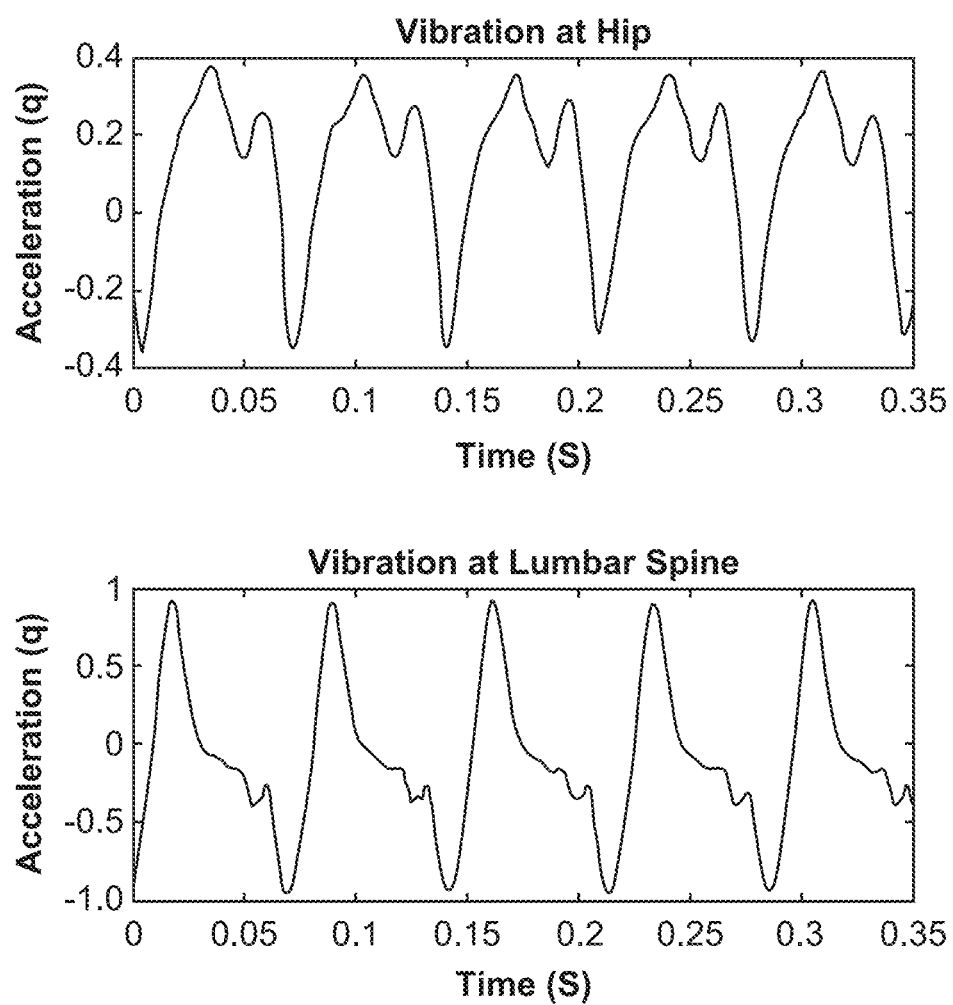

Alternatively, the present invention may also make use of feedback from accelerometers (e.g., triaxial accelerometers with a range of +/−3 g such as ADXL335, Analog Devices) to adjust the amplitude of acceleration delivered to the patient. These accelerometers (which are in communication with a processor, not shown) may be between the vibrating element 12 and user's skin or in proximity to the vibrating element 12. Once the accelerometers are secured, the peak-to-peak acceleration may be measured or monitored at, e.g., the hip (superficial to the right iliac crest) and lumbar spine (first lumbar vertebra), along areas of the skin not covered by the device and optionally wrapped tightly with elastic bandages to secure the attachment. An example of an accelerometer 17' which may be used with the apparatus is illustrated in FIG. 3. While a single accelerometer 17' is shown, multiple accelerometers may be utilized if so desired. Moreover, the user of accelerometers 17' may be utilized with any of the apparatus variations as described herein. FIG. 5B illustrates the accelerations experienced at the hip and lumbar spine using the accelerometers.

When turned on, the device can adjust the acceleration to the desired level and maintain it during the course of the treatment. This feature also allows for self-correcting of the pack if the straps loosen, the patient changes posture, or any other event that may impact the acceleration felt by the patient. Alternatively, the accelerometers may be a permanent part of the device. Though not as accurate as accelerometers secured directly to the skin, this method still provides useful information about the acceleration magnitude and can also be used for feedback control. An illustration of this is shown in FIG. 3, which has two pack-mounted accelerometers 17.

Figure 6:
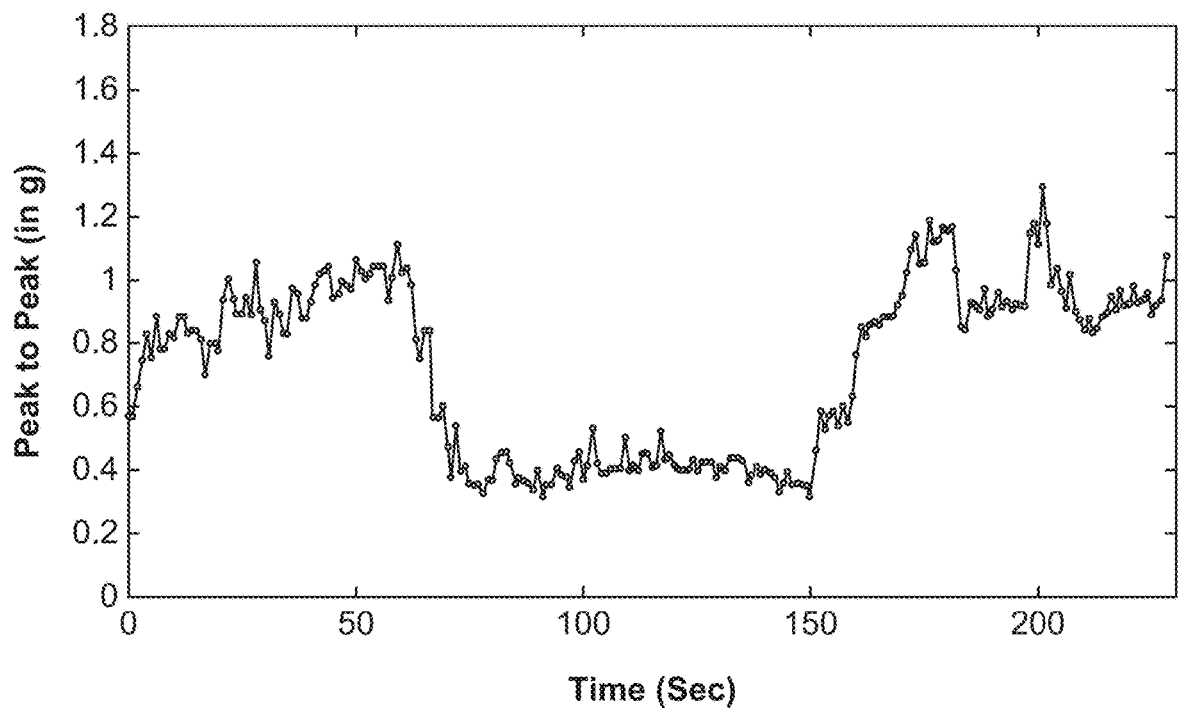
FIG. 6 is a plot demonstrating the ability of the present invention to automatically adjust the magnitude of acceleration based on accelerometer feedback.

FIG. 6 shows a plot that demonstrates the ability of the present invention to adjust the magnitude of the acceleration based on accelerometer-based feedback. At 60 seconds, the device is loosened such that the acceleration delivered to the patient has been diminished. At 150 seconds, the device automatically adjusts to the loosening by increasing the magnitude of the acceleration until it has returned to the pre-loosening level.

The present invention may also make use of force or tension sensors embedded in/on securing mechanisms 14. These sensors can provide feedback about the snugness of the device against the patient, which affects the efficiency of acceleration transmission. Preferably, the device provides an alert if the securing mechanisms are too loose, whether initially or due to loosening during a treatment session.

Figure 7:
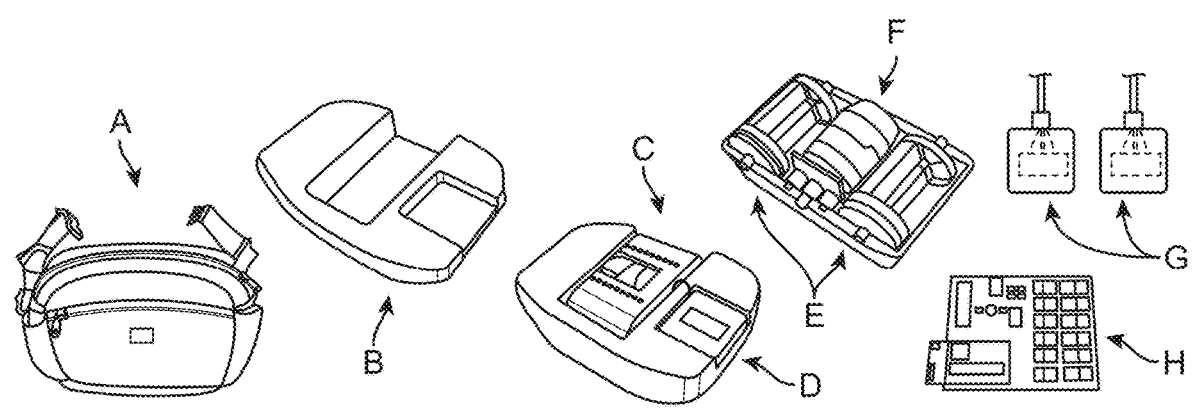
FIG. 7 is a picture of a preferred embodiment of the present invention and its components.

A preferred embodiment of the present invention is shown in FIG. 7, which illustrates the components that comprise the device. Components of the wearable vibration device include the waist-pack housing A, padding B, motor housing C, battery D, eccentric weights E, DC motor F, surface mount electrodes G, and computer chip with control software H.

The method and apparatus of the present invention enable the treatment and prevention of osteoporosis in an individual in a standing, seated or any other upright static posture, as well as during ambulation or any other activities of daily living, such as driving a car, driving an electric wheelchair, or riding a train. Other advantages provided by the method and apparatus of the present invention include the direct application of repeated mechanical loads to the bones most at risk for fracture in osteoporosis, and bypassing the unnecessary mechanical loading of the feet or knees as is done in vibrational platforms. Another advantage of the method and apparatus of the present invention is that little or no training/learning is required of an individual to utilize the present invention.

Additionally, the present invention provides the advantage of having the potential to deliver vibration stimulus to the spine and hips in more than just an inferior-superior direction (but also transverse, or side-to-side, and front-to-back directions).

Although the present invention has been described with respect to preferred embodiments, it will be readily apparent to those having ordinary skill in the art to which it appertains that changes and modifications may be made thereto without departing from the spirit or scope of the disclosure.

What is more, the wearable nature of the present invention provides for portable and battery-powered delivery systems for WBV, an issue not contemplated in the current state of the art for vibration treatment systems.

In addition, one embodiment of the present invention would include a mechanism for delivering WBV through a bicycle (e.g. stem, seat, pedals, handlebars) to support/preserve BMD in cyclists.

Additionally, the present invention is intended to be used for the purpose of providing a wearable tool for weight loss, decreasing waist circumference and decreasing adipogenesis.

The applications of the devices and methods discussed above are not limited to the treatment of bone loss but may include any number of further treatment applications. Moreover, such devices and methods may be applied to other treatment sites within the body. Modification of the above-described assemblies and methods for carrying out the invention, combinations between different variations as practicable, and variations of aspects of the invention that are obvious to those of skill in the art are intended to be within the scope of the claims.

What is claimed is:

1. A wearable apparatus for preserving or improving bone density, simulating bone growth, preserving or improving bone strength, or inhibiting adipogenesis, comprising:
   one or more vibrating elements configured for imparting repeated mechanical loads to an area of bone of an individual at a frequency and acceleration sufficient for preserving or improving bone density, simulating bone growth, preserving or improving bone strength, or inhibiting adipogenesis, wherein the one or more vibrating elements are configured to be secured to the individual such that vibrations from the repeated mechanical loads are carried through the body to bones beyond the first region;
   one or more securing mechanisms configured for securing the one or more vibrating elements to the area of bone;
   one or more accelerometers configured to be attached to the apparatus and measure an acceleration imparted by the one or more vibrating elements; and
   an electronics assembly in communication with the one or more accelerometers, wherein the electronics assembly is further configured to track and/or report compliance of use with a prescribed or recommended usage in accordance with preserving or improving bone density, simulating bone growth, preserving or improving bone strength, or inhibiting adipogenesis.

2. The apparatus of claim 1 wherein the one or more accelerometers are positionable over the area of bone.

3. The apparatus of claim 1 wherein the one or more accelerometers are locatable at a distance from the area of bone.

4. The apparatus of claim 1 wherein the electronics assembly is further configured to log a use of the apparatus by the individual.

5. The apparatus of claim 1 further comprising a timer in communication with the electronics assembly and where the timer is configured to track a length of a treatment.

6. The apparatus of claim 1 wherein the electronics assembly is further configured to provide one or more treatment session reminders to the individual.

7. The apparatus of claim 1 wherein the one or more vibrating elements are configured to impart repeated mechanical loads to a hip, femur and/or spine of the individual.

8. The apparatus of claim 1 wherein the one or more vibrating elements are configured for impart repeated mechanical loads to a sacrum or coccyx of the individual.

9. A method for preserving or improving bone density, simulating bone growth, preserving or improving bone strength, or inhibiting adipogenesis, comprising:
   providing one or more vibrating elements for securement to an area of bone of a body of an individual;
   imparting repeated mechanical loads to the area of bone via the one or more vibrating elements at a frequency and acceleration sufficient for preserving or improving bone density, simulating bone growth, preserving or improving bone strength, or inhibiting adipogenesis such that vibrations from the repeated mechanical loads are carried through the body to bones beyond the area of bone;
   measuring acceleration imparted by the one or more vibrating elements via one or more accelerometers; and
   tracking and/or reporting compliance of use with a prescribed or recommended usage in accordance with preserving or improving bone density, simulating bone growth, preserving or improving bone strength, or inhibiting adipogenesis via an electronics assembly which is also in communication with the one or more accelerometers.

10. The method of claim 9 wherein measuring acceleration comprises measuring the acceleration at the area of bone.

11. The method of claim 9 wherein measuring acceleration comprises measuring the acceleration at a distance from the area of bone.

12. The method of claim 9 further comprising logging a use of the apparatus by the individual via the electronics assembly.

13. The method of claim 9 further comprising tracking a length of a treatment via a timer in communication with the electronics assembly.

14. The method of claim 9 further comprising providing one or more treatment session reminders to the individual via the electronics assembly.

15. The method of claim 9 wherein imparting the repeated mechanical loads comprises imparting the repeated mechanical loads to a hip, femur and/or spine of the individual.

16. The method of claim 9 wherein imparting the repeated mechanical loads comprises imparting the repeated mechanical loads to a sacrum or coccyx of the individual.

* * * * *